(12) United States Patent
Vardi

(10) Patent No.: US 11,737,669 B2
(45) Date of Patent: Aug. 29, 2023

(54) SYSTEM AND METHOD FOR REMOTE MONITORING OF A USER'S VITAL SIGNS AND BODILY FUNCTIONS

(71) Applicant: ETROG SYSTEMS LTD., Jerusalem (IL)

(72) Inventor: Eyal Dov Vardi, Bet-Nir (IL)

(73) Assignee: ETROG SYSTEMS LTD., Jerusalem (IL)

(*) Notice: Subject to any disclaimer, the term of this patent is extended or adjusted under 35 U.S.C. 154(b) by 0 days.

(21) Appl. No.: 17/480,524

(22) Filed: Sep. 21, 2021

(65) Prior Publication Data

US 2022/0000366 A1 Jan. 6, 2022

Related U.S. Application Data

(63) Continuation of application No. 16/356,680, filed on Mar. 18, 2019, now Pat. No. 11,154,195.

(60) Provisional application No. 62/643,912, filed on Mar. 16, 2018.

(51) Int. Cl.
| | | |
|---|---|---|
| A61B 5/00 | (2006.01) | |
| A61B 5/024 | (2006.01) | |
| A61B 5/0205 | (2006.01) | |
| A61B 5/11 | (2006.01) | |
| G08B 21/04 | (2006.01) | |
| A61B 5/318 | (2021.01) | |

(52) U.S. Cl.
CPC .......... *A61B 5/0022* (2013.01); *A61B 5/0006* (2013.01); *A61B 5/0008* (2013.01); *A61B 5/0205* (2013.01); *A61B 5/02416* (2013.01); *A61B 5/4815* (2013.01); *A61B 5/6822* (2013.01); *A61B 5/7275* (2013.01); *A61B 5/0024* (2013.01); *A61B 5/1102* (2013.01); *A61B 5/318* (2021.01); *A61B 5/6802* (2013.01); *A61B 5/6831* (2013.01); *A61B 5/747* (2013.01); *A61B 2562/0219* (2013.01); *G08B 21/0453* (2013.01)

(58) Field of Classification Search
CPC ... A61B 5/0022; A61B 5/0006; A61B 5/0008; A61B 5/0205; A61B 5/02416; A61B 5/4815; A61B 5/6822; A61B 5/7275; A61B 5/0024; A61B 5/1102; A61B 5/318; A61B 5/6802; A61B 5/6831; A61B 5/747; A61B 2562/0219; A61B 5/6832; A61B 2560/0456; A61B 5/02055; A61B 5/02427; A61B 5/02438; A61B 5/14552; A61B 5/282; G08B 21/0453; G08B 25/016; G08B 29/20; G16H 40/67; G16H 80/00
USPC ...................................................... 340/573.14
See application file for complete search history.

(56) References Cited

U.S. PATENT DOCUMENTS

| | | | | |
|---|---|---|---|---|
| 6,471,087 B1* | 10/2002 | Shusterman | ......... | A61B 5/6805 600/300 |
| 10,610,153 B2* | 4/2020 | Auphan | ............... | G01G 19/445 |
| 2011/0066043 A1* | 3/2011 | Banet | ...................... | A61M 1/14 600/485 |

(Continued)

*Primary Examiner* — Omar Casillashernandez
(74) *Attorney, Agent, or Firm* — Amster, Rothstein & Ebenstein LLP

(57) ABSTRACT

A system and method for comprehensive remote monitoring of a user's vital signs and bodily functions includes a wearable monitor in bi-directional communication with a gateway element that communicates with one or more external devices to allow remote access to user vital sign and bodily function information.

22 Claims, 17 Drawing Sheets

(56) References Cited

U.S. PATENT DOCUMENTS

| | | | |
|---|---|---|---|
| 2016/0314672 A1* | 10/2016 | Wiggermann | A61B 5/1117 |
| 2016/0330573 A1* | 11/2016 | Masoud | H04W 12/0431 |
| 2016/0338891 A1* | 11/2016 | Agdeppa | G16H 10/60 |
| 2017/0056682 A1 | 3/2017 | Kumar et al. | |
| 2017/0246041 A1 | 8/2017 | Cumming et al. | |
| 2018/0055382 A1 | 3/2018 | Woodward et al. | |
| 2018/0168460 A1* | 6/2018 | Morris | A61B 5/7221 |
| 2019/0070419 A1* | 3/2019 | Virtanen | A61N 1/36521 |
| 2019/0080056 A1* | 3/2019 | Das | A61B 5/7282 |
| 2022/0313515 A1* | 10/2022 | Williams | G16H 40/20 |

\* cited by examiner

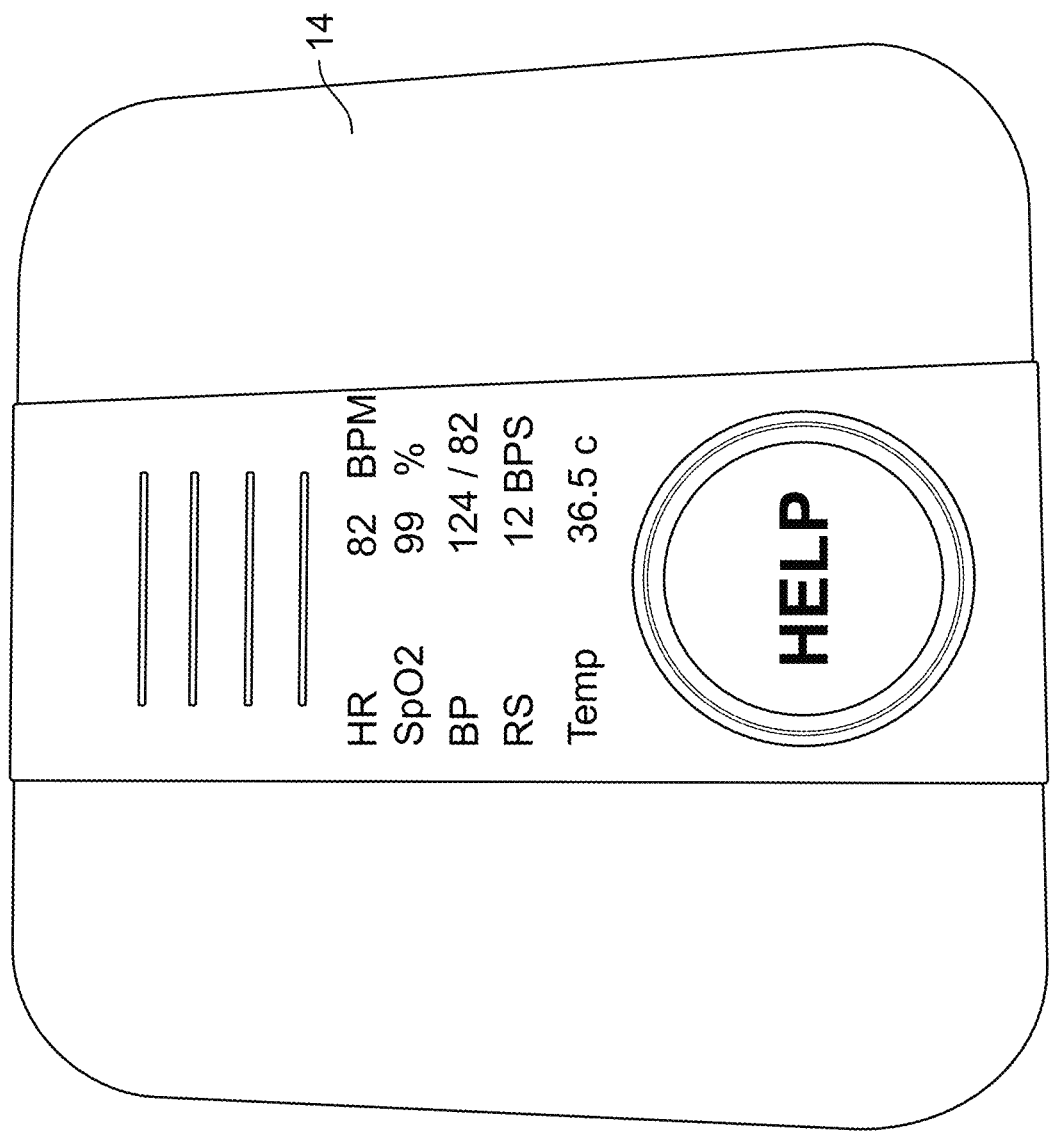

Types

| type | character | examples |
|---|---|---|
| Continued | Does not remit | Typhoid fever, typhus, drug fever, malignant hyperthermia. |
| Intermittent | Temperature falls to normal everyday | Pyogenic infection, lymphoma, military T.B. |
| Remittent | Daily fluctuation >2c .temperature does not return to normal | Not characteristic for any particular disease. |
| Relapsing | Temperature returns to normal for days before rising again | Malaria: tertian-3days pattern, fever peaks every other day (plas. Vivax, plas.ovale), quatrain-4day pattern , fever peaks every third day (p.malaria) lymphoma: HODJKIN lymphoma Pyogenic infection | www.smso.net

FIG. 15

SYSTEM AND METHOD FOR REMOTE MONITORING OF A USER'S VITAL SIGNS AND BODILY FUNCTIONS

CROSS-REFERENCE TO RELATED APPLICATIONS

The present application is a continuation of U.S. patent application Ser. No. 16/356,680, filed Mar. 18, 2019, which claims benefit of and priority to U.S. Provisional Patent Application No. 62/643,912, filed Mar. 16, 2018 and entitled SYSTEM AND METHOD FOR REMOTE MONITORING OF A USER'S VITAL SIGNS AND BODILY FUNCTIONS, the entire content of which is hereby incorporated by reference herein.

BACKGROUND

Field of the Disclosure

The present invention relates to the remote monitoring of a user's vital signs and other bodily functions and in particular to a system and method for remote monitoring accessible by third parties.

Related Art

Healthcare costs have dramatically risen over the last several years. In particular, hospital stays have become more and more expensive making it difficult for patients who require close monitoring such as that available in a hospital setting to afford this type of care. While some such patients can be released to their homes, in order to provide the monitoring they need, it is necessary to provide sometimes equally expensive home healthcare providers. Remote monitoring and access to a user's vital signs may also be useful in other areas, such as athletics.

Accordingly, it would be beneficial to provide a system and method for providing comprehensive monitoring of vital signs and other bodily functions that allows remote access and bi-directional communication.

SUMMARY

It is an object of the present disclosure to provide a method and system to provide comprehensive monitoring of a user's vital signs and bodily functions. The method and system may be used in-home for a single or limited number of patients or users or may be provided in an enterprise environment for monitoring a plurality of patients or users. The system may also be used to monitor users in other environments as well.

A system to monitor a user's health in accordance with an embodiment of the present disclosure includes a monitor element in contact with the user's body, the monitor element including at least one sensor providing information associated with health of the user, the sensor providing information associated with one or more of: user heart rate; user respiration rate; user blood pressure; user oxygen level; a gateway element, in wireless communication with the monitor element, wherein the information associated with health of the user is received by the gateway element from the monitor element; and a central station in communication with the gateway element, wherein the information associated with health of the user is received by the central station from the gateway element, wherein the central station analyzes the information and determines whether intervention is appropriate, based at least on: at least one heartrate threshold; at least one respiration rate threshold; at least one blood pressure threshold; and at least one oxygen level threshold.

BRIEF DESCRIPTION OF THE DRAWINGS

The above and related objects, features and advantages of the present disclosure will be more fully understood by reference to the following, detailed description of the preferred, albeit illustrative, embodiment of the present invention when taken in conjunction with the accompanying figures, wherein:

FIG. 6A illustrates another exemplary embodiment of a gateway device used in the system of FIG. 1 in accordance with an embodiment of the present disclosure;

FIG. 15 illustrates a table associating fever patters with diseases; and

DETAILED DESCRIPTION OF THE EXEMPLARY EMBODIMENTS

Figure 1:
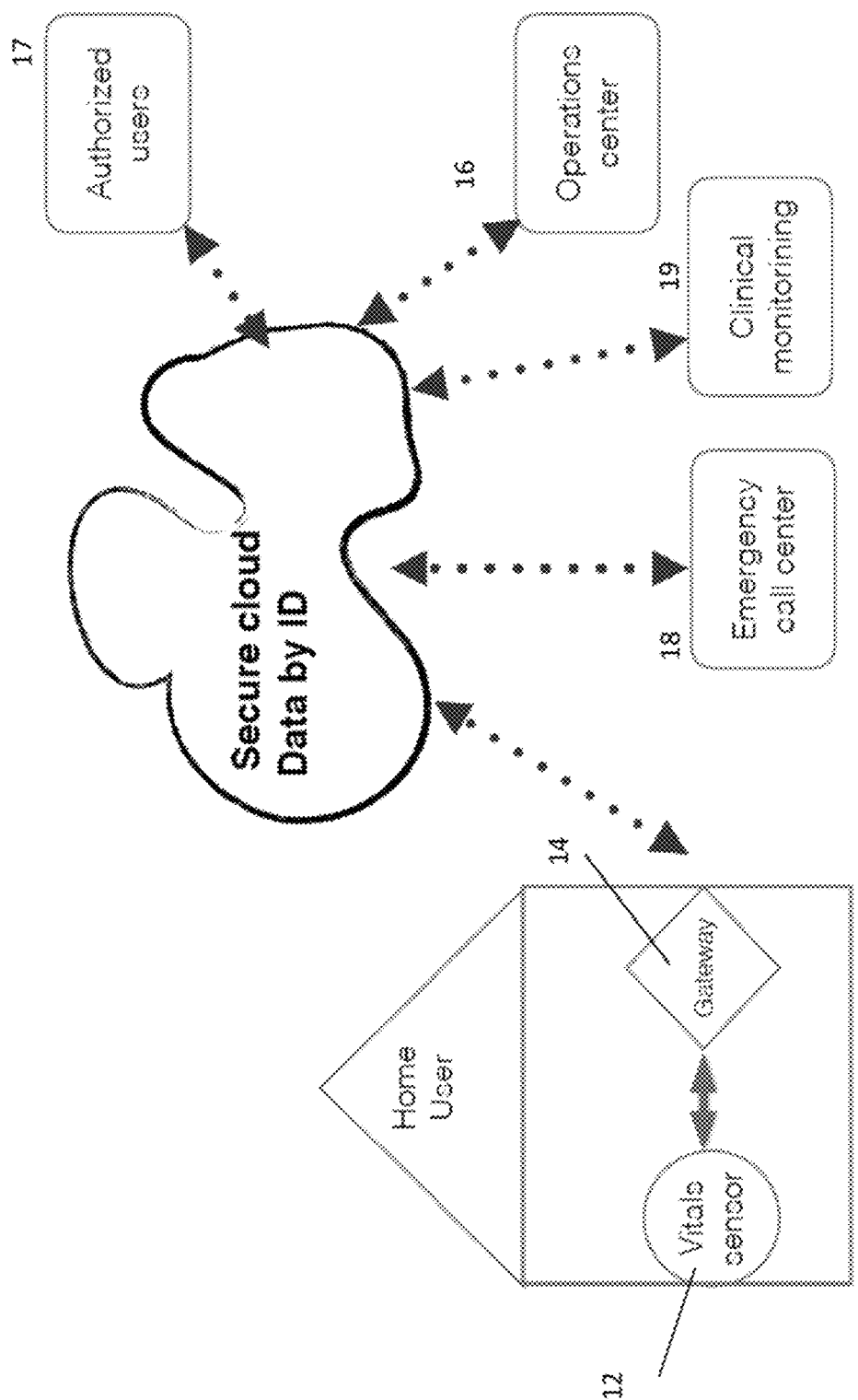
FIG. 1 illustrates an exemplary block diagram illustrating a system for monitoring a user in accordance with an exemplary embodiment of the present disclosure.

The method and system of the present disclosure relate generally to monitoring user vital signs and other bodily functions for healthcare purposes. In embodiments, vital signs may include, but are not limited to heart rate, temperature, oxygen saturation, respiratory rate and blood pressure, to name a few. More specifically, the present disclosure relates to a system and method for monitoring patient general health and well-being that allows for monitoring, storing and accessing healthcare information remotely. In an embodiment, the system and method of the present application may be used to accelerate a patient's return home from the hospital by allowing medical professionals to remotely monitor the patient while not requiring the patient to stay in the hospital which reduces costs and frees up space in hospitals.

In embodiments, the system and method of the present disclosure may also be used for other applications. For example, in embodiments, the system and method of the present disclosure may be used to allow for remote consultations with doctors or other health professionals without the need for a face to face office visit by providing real-time and historical information regarding the patient's vitals to the doctor or healthcare professional remotely. While the vital information is used herein, the information that is collected and analyzed in the system and method disclosed herein may include other health related information such as activity levels, weight and sleep patterns. Alternatively, in embodiments, the system and method of the present application may be used in an enterprise setting, such as a hospital, nursing home or rehabilitation center to monitor and retain records for a large number of patients.

While the system and method may be used for patients under a physician's care, in embodiments, it may be used in a wide variety of other applications. For example, the ability to remotely monitor a user's vital signs and other bodily functions is may also be useful in athletics. In embodiments, monitoring player vital signs and bodily functions and allowing other parties to access the data allows for players to improve training and performance by allowing coaches, trainers, doctors, etc. to access their body's condition during and after activity. This information may be used to maximize player performance and/or to monitor player health after an injury. In addition, in embodiments, routine monitoring of vital signs and other bodily functions may also be useful for users who are in general good health and are not currently under the care of a physician as a means to maintain good health. In embodiments, routine monitoring of user health may be useful in identifying variations in bodily functions or vital signs that may be an early sign of disease or disorder such that any such problem can be diagnosed or treated early. Early treatment of many diseases or disorders greatly increases the chances of cure and often at the very least, minimizes damage to the body. Thus, the method and system of the present disclosure may be used by a variety of different users in different environments as desired.

In an embodiment, the system 10 of the present disclosure preferably includes a wearable monitor 12 that is in wireless communication with a gateway device or element 14. FIG. 1 illustrates an embodiment in which a single patient or user is monitored in a home setting. In an enterprise setting, in embodiments, multiple gateway devices 14 would preferably be provided throughout a hospital or other institution. In embodiments, multiple monitoring devices or elements 12 may be provided, each one associated with a single patient or user. In embodiments, the multiple gateways 14 may be used to determine a location of a particular patient or user in the facility based. In embodiments, a location of a monitoring device 12, and the patient associated therewith, may be determined by its communication with particular gateway device 14. In embodiments, the gateway device 14 preferably wirelessly communicates with external devices and entities, such as a central monitoring station 16, for example. In embodiments, the gateway device 14 may also communicate with an emergency call center 18. In an embodiment, the gateway device 14 may also communicate with a clinical monitoring center 19. In embodiments, the gateway device 14 sends information to and receives information or instructions from one or more computing device associated with the central monitoring station 16, emergency call center 18 and/or clinical monitoring center 20. In embodiments, the computing device may be any desired computing device, including but not limited to a smart phone including a software application including computer executable instructions to access and view data in the system 10. If desired, other authorized users 17 may communicate with the gateway device 14 as well. These other users may include individual healthcare providers, insurance companies or agents thereof and/or family members of the patient. In embodiments, all communication is bi-directional such that the monitor element 12 and the gateway device 14 transmit and receive information. In an embodiment, communication between the monitor 12 and the gateway 14 is wireless and may use any desired protocol including radio frequency communication as well as optical and/or ultrasonic communication. In a preferred embodiment, the gateway 14 communicates using more than one radio frequency to provide for redundancy to external entities. In embodiments, the gateway 14 may also communicate via wire as well with the central monitoring station 16, emergency call center 18 and clinical monitoring center 19. In embodiments, the gateway 14 may communicate with the central monitoring station 16, emergency call center 18 and clinical monitoring center 19 using any suitable or desired protocol and hardware, including but not limited to PSTN.

In embodiments, the wearable monitor 12 may include a plurality of sensor elements that are used to monitor different patient health functions. In embodiments, the monitor 12 may include a plurality of sensors that gather information sufficient to calculate or otherwise determine information indicative of the user's vital signs and other bodily functions. In embodiments, these calculations may take place in the monitor 12, in the gateway 14 or in any of the central monitoring station 16, emergency call center 18 and clinical monitoring center 19.

Figure 2:
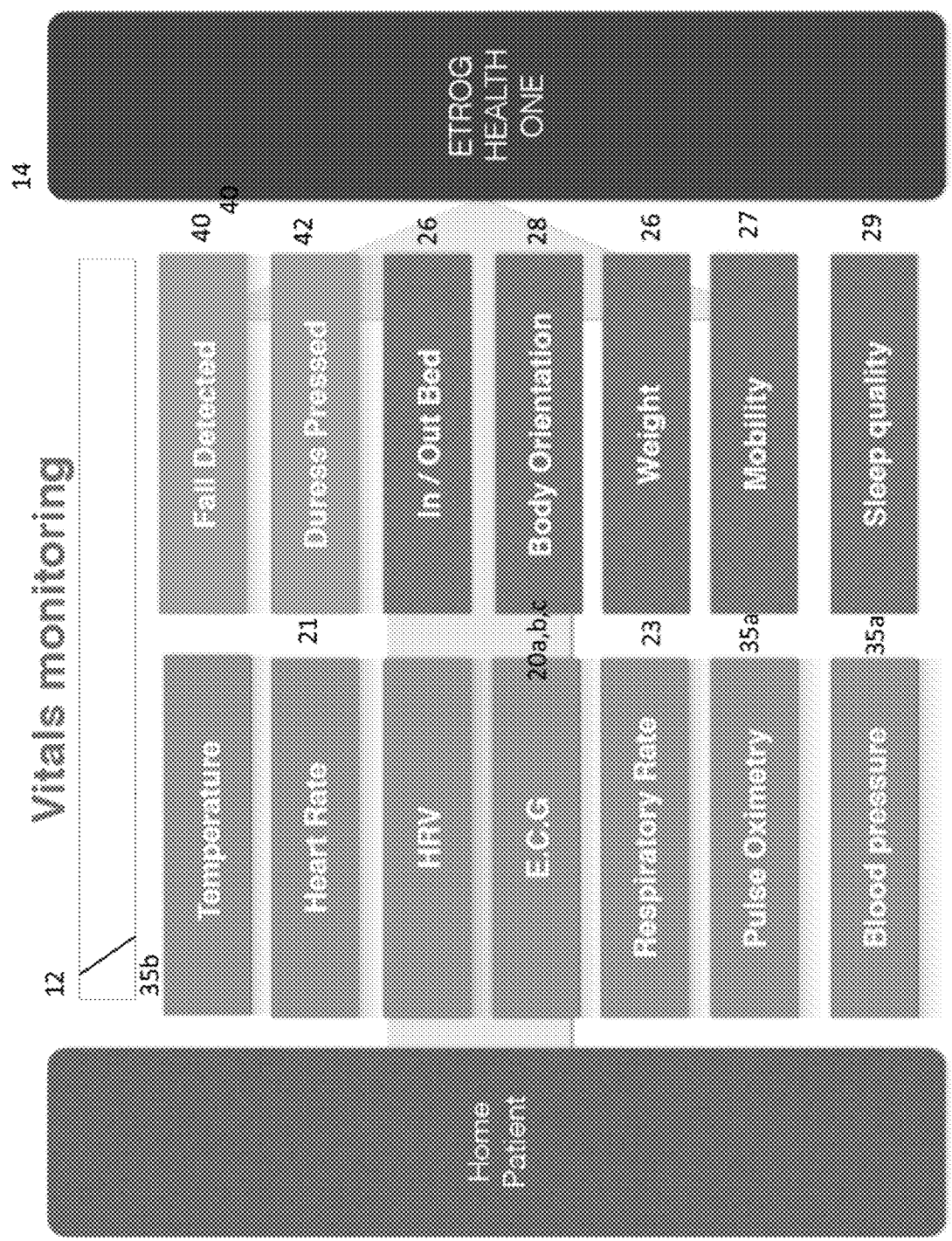
FIG. 2 illustrates a schematic representation of the vital signs and bodily functions of the user monitored in the system of FIG. 1 in accordance with an exemplary embodiment of the present disclosure.

FIG. 2 illustrates the different categories of vital sign and bodily function information that may be provided based on the information gathered by the monitor 12. In embodiments, the wearable monitor 12 may include a temperature sensor 20 to provide an indication of the patient's body temperature. In embodiments, the wearable monitor 12 also preferably includes receptacles 20a, 20b, 20c which are connectable to one or more electrodes E (see FIG. 12, for example) that may be used for an electro cardiogram (ECG). In embodiments, the wearable monitor 12 may also provide blood pressure information 24 as well as a pulse oximetry information 25. In embodiments, mobility information 27 may also be provided as an indication of patient mobility. In embodiments, information regarding orientation 28 may be used to indicate the patient's orientation in bed. In embodiments, sleep quality information 29 may be provided as an indication of the patient's quality of sleep. In embodiments, the sensors used to provide this information are preferably all included in the monitoring device 12 which is connected to the patient.

In embodiments, the system 10 preferable includes other monitors or sensors as well. In embodiments, a scale 26 may be incorporated into the patient's bed to provide an indication of the patient's weight, and provide this information to the gateway 14, either directly or via the wearable monitor 12. In embodiments, the scale 26 may also be used to determine whether the user is in the bed or not. In embodiments, the scale 26 may be embodied as a conventional scale including a wireless transmission element such that it can communicate weight information to gateway 14. In embodiments, a heart rate monitor 21 may be provided to record the patient's heart rate and is preferably provided in the user's bed. In embodiments, a respiratory sensor 23 is also preferably provided in the user's bed and provides an indication of the patient's respiratory rate. These components may be provided separately or integrated together in the in-bed monitoring element 90 discussed below, for example. In embodiments, all of the sensors discussed above provide information about the patient that is keyed to a common time code such that data regarding all parameters of the user's health at a particular time can be linked, recorded, viewed and retrieved.

Figure 10:
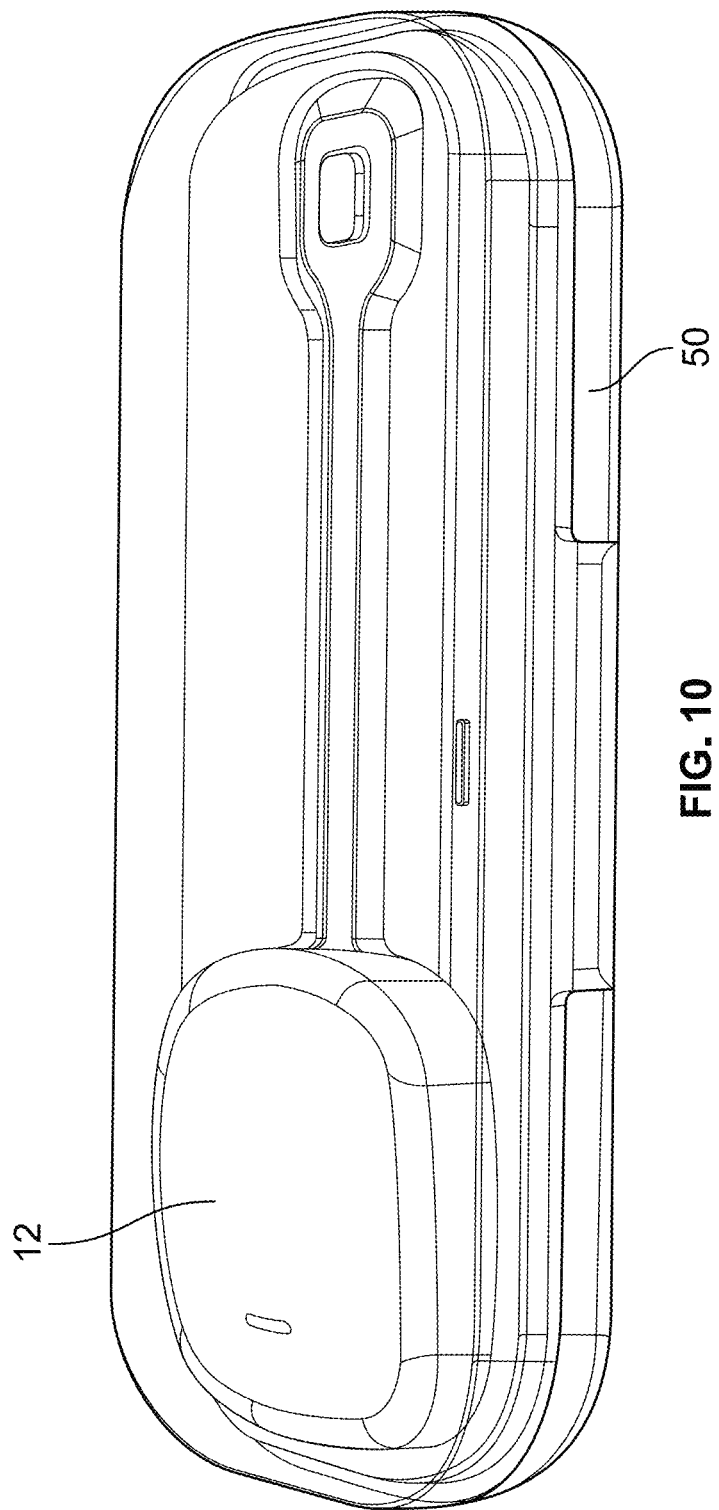
FIG. 10 illustrates an exemplary embodiment of a charging cradle for use in recharging the monitor of FIGS. 3A-3C.

In embodiments, the monitor 12 may be waterproof and is preferably rechargeable. FIG. 10 illustrates an exemplary recharging cradle 50 in which the monitor 12 may be placed for recharging. In embodiments, the recharging cradle 50 may be connected to a power source and also may include a battery such that it can be used to recharge the monitor 12 even in the event of a power failure. In embodiments, the monitor 12 may include charging leads (not shown) for connection to the charging cradle 50. In embodiments, the monitor 12 may include wireless recharging features such that it may be recharged when placed in close proximity to the cradle 50, or simply placed in the cradle 50.

In an embodiment, heart rate, respiratory rate, bed occupancy and sleep monitoring may also be provided by a separate in-bed monitoring element 90. In embodiments, the in-bed monitoring element 90 may be used in addition to the monitor 12 and transmits information to the gateway 14. In embodiments, the in-bed monitoring element 90 is not in contact with the patient's body. In embodiments, the in-bed monitoring element 90 may use ballistocardiography to sense motion changes of the patient which may be used to determine heart rate and respirator rate as well as motion. In embodiments, the monitor 12 may also be used to gather some of the information gathered by the in-bed monitoring element 90, including at least heart rate and respiratory rate information. In embodiments, overlapping information collection may be used to improve accuracy of the monitors 12 and 90 as well as the accuracy of the system 10 as a whole.

Figure 13:
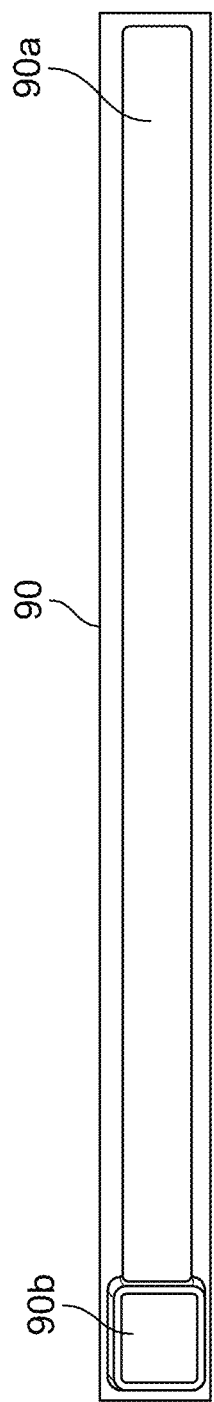
FIG. 13 illustrates an exemplary in-bed monitor suitable for use in the system of FIG. 1.

In embodiments, all of the information gathered, regardless of whether it is gathered by monitor 12 or monitoring element 90, may be time coded such that it may properly correlated when processed to reflect patient health at the same time. FIG. 13 illustrates an exemplary embodiment of the in-bed monitoring element 90 in which the monitoring element includes a sensing portion 90a and a wireless transmitting portion 90b to transmit information to the gateway 14.

In an embodiment, each patient or user may be uniquely identified based on data collected by the wearable monitor 12. In an embodiment, on an initial use, the monitor 12 may gather information about the user's health that is provided to the gateway 14 and used to generate a unique body signature for the individual patient. In embodiments, this signature may be generated by the monitor 12, the gateway 14, or at a central monitoring station 16. In embodiments, the unique body signature may be based on a variety of information gathered by the sensors of the monitor 12 along with other security measures to provide an encrypted signature unique to the user. In embodiments, once this signature is created, it may be stored and each time the monitor 12 is connected to a patient or user, that patient's monitored information will be compared to the unique signature. In embodiments, if there is no match, an alert signal may be provided to indicate that there is a problem or possible fraud. In embodiments, this unique signature may be provided in the calibration step discussed below.

Figure 7:
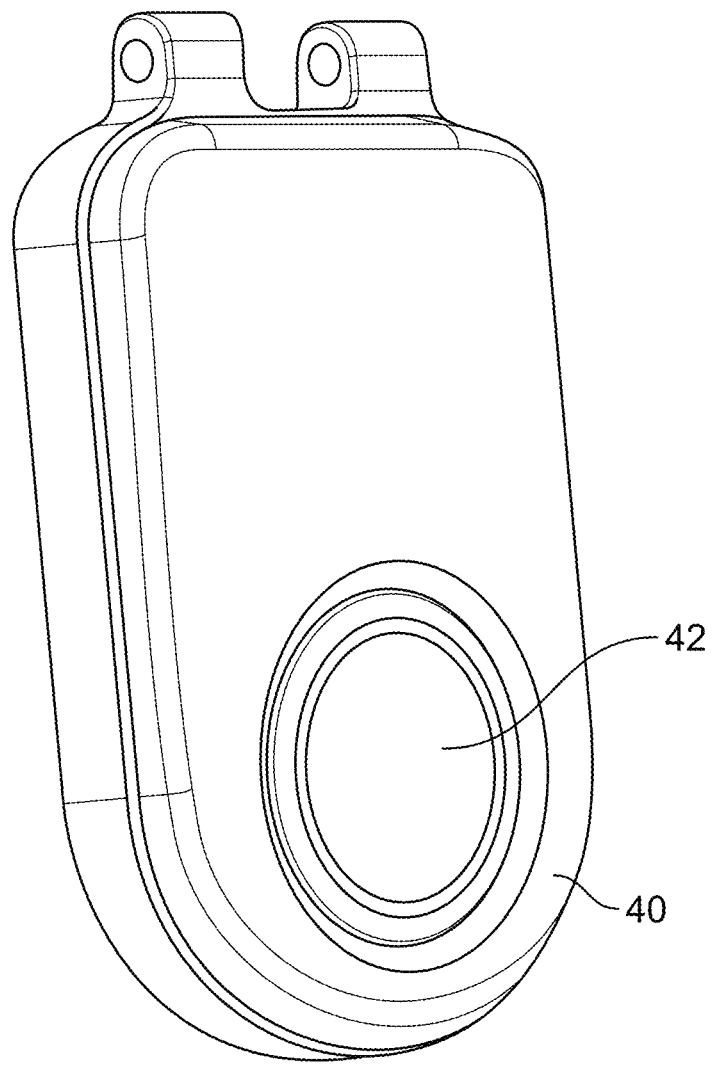
FIG. 7 is an exemplary embodiment of a pendant worn by a user and in communication with the gateway device of the system of FIG. 1 in accordance with an embodiment of the present disclosure.

In an embodiment, the system 10 may also include a pendant device 40 (see FIG. 7), preferably worn around the patient's neck. The pendant device 40, however, may be worn elsewhere or otherwise carried by the patient. In embodiments, while the pendant device 40 should always stay with the user, it should be free to move while on the user. In contrast, in embodiments, the wearable monitor 12 is preferable adhered to the user's skin and stays substantially in the same place while being worn. In an embodiment, the pendant device 40 may include an alert or duress button 42 or other indicator that may be activated by the patient when they are in duress. In embodiments, activation of this indicator transmits a duress signal, or alert signal, which is preferably received by gateway 14, which in turn contacts the emergency call center 18. In embodiments, upon receipt of the duress/alert signal, the call center 18 may provide emergency assistance and/or may contact a health care provider or others to intervene. In embodiments, since communication between the gateway 14 and call center 18 is bidirectional, voice communication may be established between the call center and the patient such that the patient may be interrogated about the cause of distress and a decision may be made about whether intervention is necessary. In embodiments, the call center 18 may provide emergency assistance by contacting local police or fire department to send first responders to aid the patient and/or may contact health care providers in the hospital or home. In embodiments, the call center 18 may also contact the patient's family members or designated emergency contact, if desired. In embodiments the decision and communications discussed above may be made by the central station 16 or the clinical monitoring station 19.

In embodiments, the pendant 40 may include an accelerometer (not shown) which may be used to detect the occurrence of a user fall. In embodiments, in the event of such a fall, the pendant 40 may also transmit the duress/alert signal. In embodiments, the duress/alert signal may be conveyed to the emergency call center 18 as noted above. In an embodiment, the pendant 40 will communicate with the gateway 14 which will then contact the call center 18. In embodiment, the pendant 40 may contact the call center 18 directly. The pendant 40 preferably provided bidirectional communication to the call center 18, either through the gateway 14 or directly, for example, to allow the user to confer with emergency dispatchers and/or medical personnel.

Figure 3A:
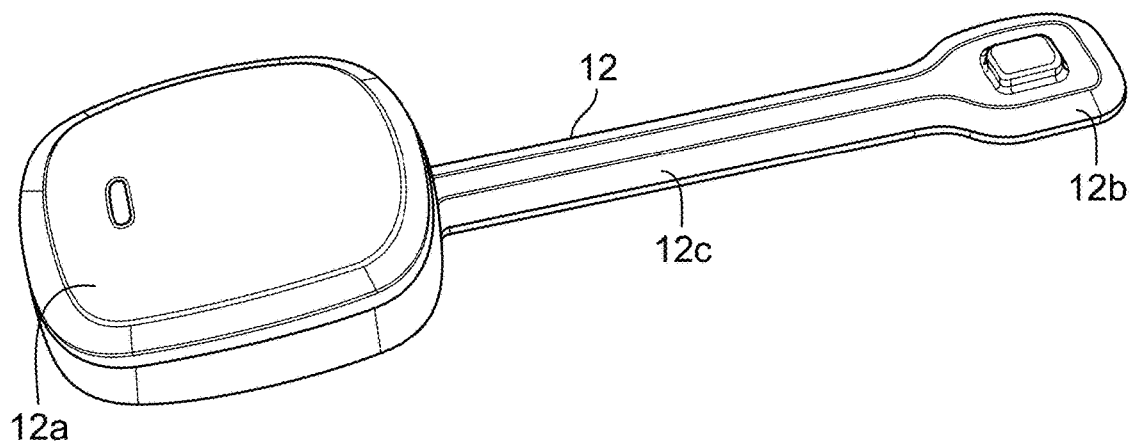
FIGS. 3A, 3B and 3C illustrate an exemplary embodiment of a wearable monitor suitable for use in the system of FIG. 1 in accordance with an exemplary embodiment of the present disclosure.
Figure 3B:
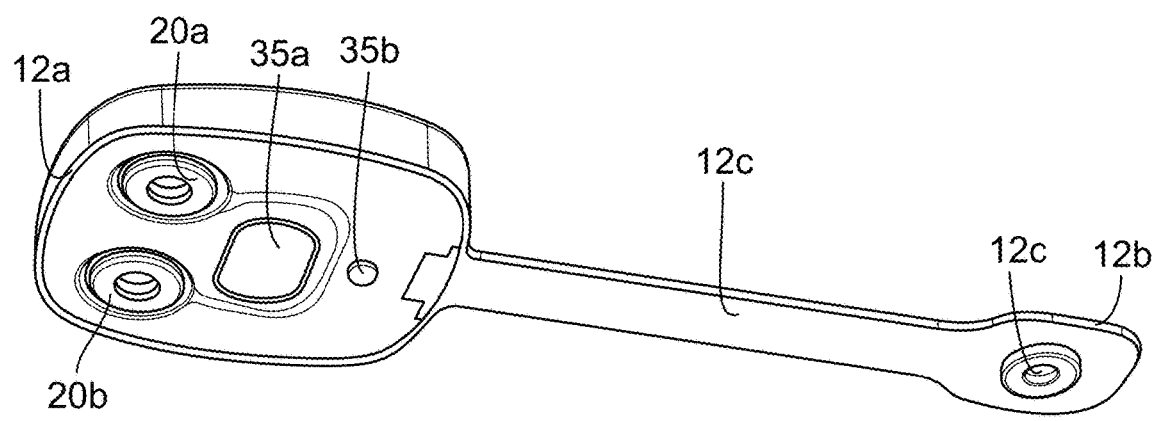
Figure 3C:
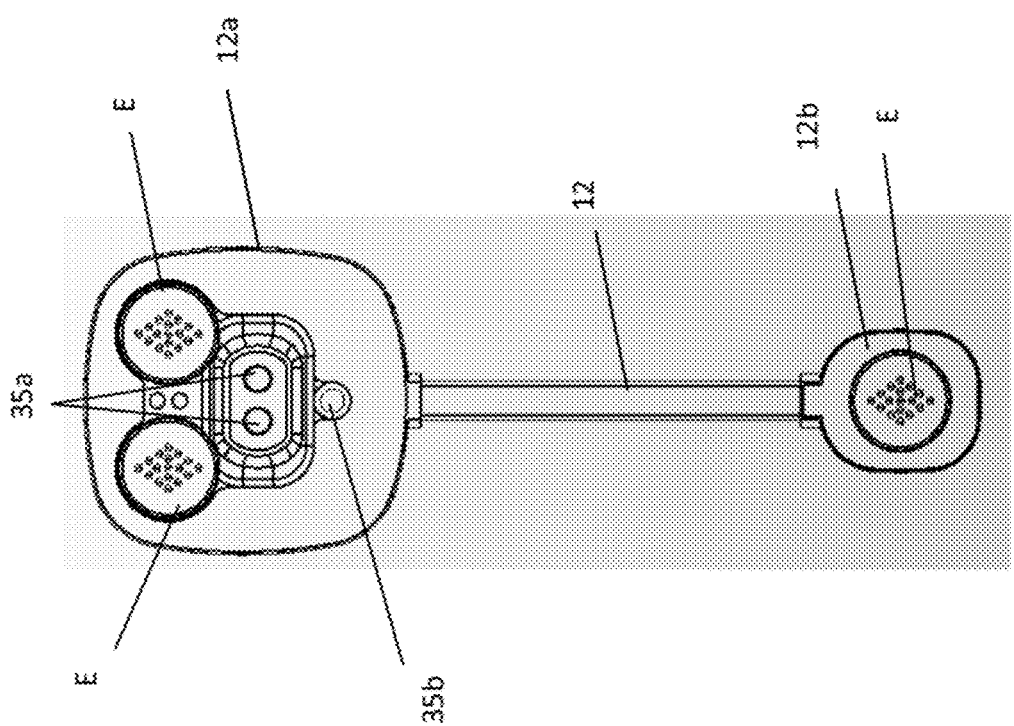

The wearable monitor 12 is illustrated in further detail in FIGS. 3A-3C. In embodiments, the monitor 12 preferably includes electrode receptacles 20a, 20b and 20c (see FIG. 3B) that accommodate electrodes E (see FIG. 3C). In a preferred embodiment, these electrode receptacles are used with "dry electrodes" in that they do not require the use of a conductive gel or other conductive substance to operate. Conventional electrodes such as those used for ECG's are usually "wet electrodes" in that a conductive gel material is applied to the user's skin to ensure good contact and avoid noise during ECG readings. Unfortunately, these conductive gels and other materials are not suitable to remain on the patient's skin for long periods of time since the salts in these materials have a tendency to irritate skin. Since monitor 12 is intended to be worn substantially constantly by a patient for long periods of time, wet electrodes are simply not a good option, although, it is noted that wet electrodes may be used with the monitor 12 as well. In a preferred embodiment, upon application of the monitor 12 to a user's skin, the device performs a test to determine whether the preferred dry electrodes are in use. If not, an alert is issued.

In embodiments, the wearable monitor 12 may be designed to allow for desired positioning of the electrode receptacles 20a, 20b and 20c (and the electrodes positioned therein) to provide accurate ECG results. In addition, the body of the monitor 12 may be designed to provide for relative comfort while providing opportune placement of the electrodes E. In embodiments, the monitor 12 preferably includes a main portion 12a and a smaller secondary portion 12b spaced apart from the main portion on an opposite end thereof. In embodiments, the main portion 12a and secondary portion 12b are connected to each other by a narrow and somewhat flexible bridge portion 12c. In embodiments, as a result, in embodiments, the electrode receptacles 20a, 20b and 20c may be positioned at a desired spacing while the somewhat flexible connection between the main portion 12a and secondary portion 12b allows for comfort as the user moves around during the day. In embodiments, the bridge portion 12c is somewhat flexible and not attached directly to the user's skin which increases comfort for the user such that the main portion 12a and secondary portion 12b are movable with the user's skin while the bridge 12c provides flexibility.

Figure 4:
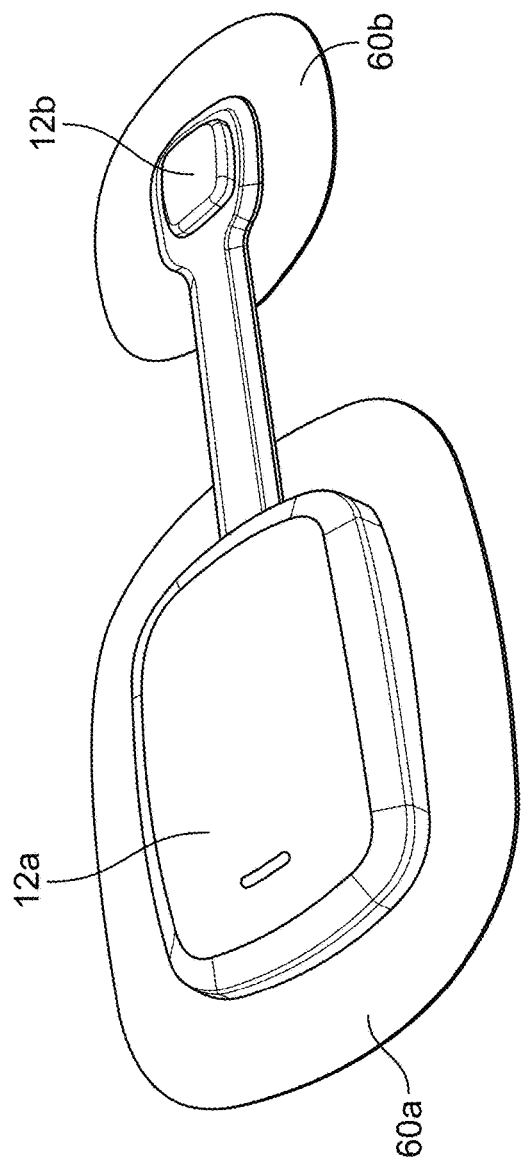
FIG. 4 illustrates the wearable monitor of FIGS. 3A-3C including an adhesive element for adhering the monitor to a patient's skin in accordance with an exemplary embodiment of the present disclosure.
Figure 5A:
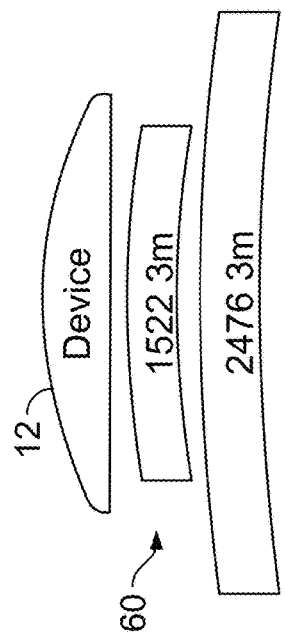
FIG. 5A illustrates an exemplary cross-section of the adhesive element of FIG. 5 connected to the monitor.
Figure 5:
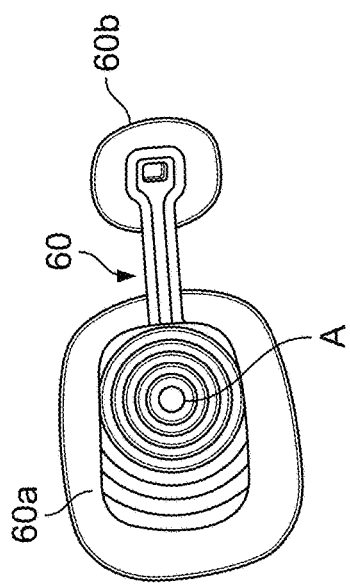
FIG. 5 is a detailed illustration of the adhesive element of FIG. 4 in accordance with an exemplary embodiment of the present disclosure.
Figure 16:
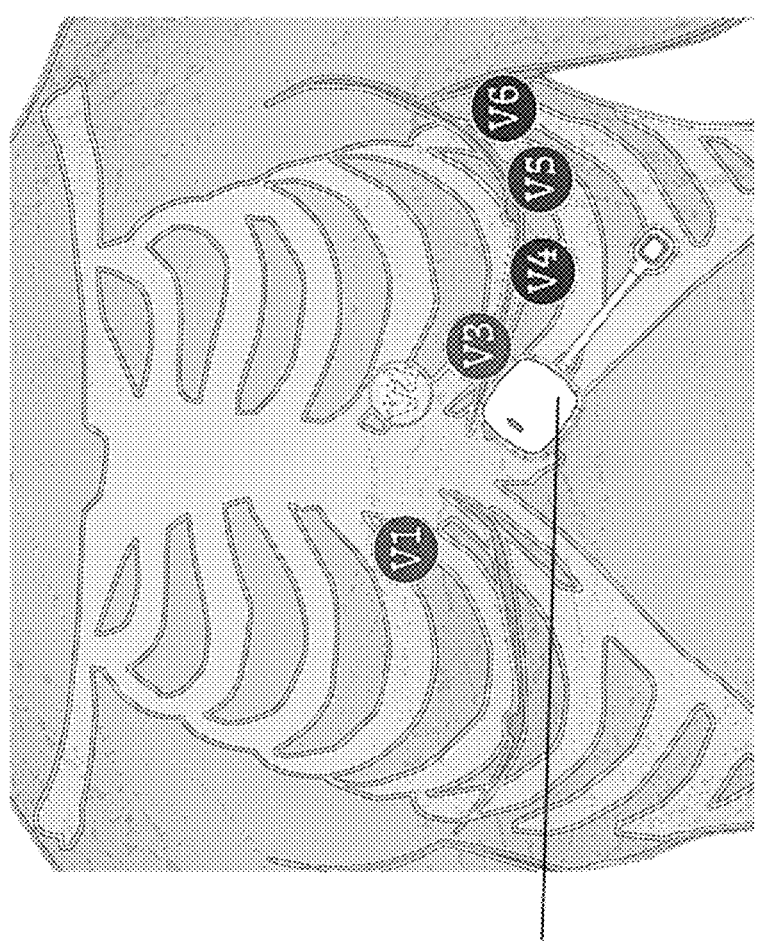
FIG. 16 illustrates an exemplary placement of the monitor of FIGS. 3A-3C on a user's chest.

The main portion 12a and secondary portion 12b are directly connected to the user's skin via adhesive element 60. In an embodiment, the adhesive element 60 may include a main part 60a and a smaller secondary part 60b. In embodiments, the main part may have an open center region and extends beyond a periphery of the main portion 12a of the monitor 12. In embodiments, the secondary part similarly has an open center portion and extends beyond a periphery of the secondary portion 12b, as can be seen in FIG. 4, for example. In embodiments, the adhesive element 60 preferably includes a lower layer of adhesive that is connected to a user's skin that is hypoallergenic and is preferably made of cloth or silicone, which tend to be less abrasive to skin and add comfort. In embodiments, another adhesive layer may be provided over the lower layer and connects to the monitor 12 which need not be hypoallergenic and may be of any desired material as it does not contact user skin. In embodiments, these multiple layers are visible in the cross-sectional view of FIG. 5A, for example. While FIG. 5A indicates specific products used in the layers, any suitable materials may be used. In embodiments, an applicator A may be provided to guide placement of the adhesive element 60 on the monitoring device 12. While the monitor 12 is preferably adhered to the user's skin, in an embodiment, the monitor 12 may be incorporated into fabric or an article of clothing and held next to the user's body. In such an embodiment, the adhesive element 60 may not be necessary. FIG. 16 illustrates an exemplary positioning of the monitor 12 on a user's chest. FIG. 16 also indicates the various lead placement locations V1, V2 . . . V6 used in conventional ECGs.

Figure 12:
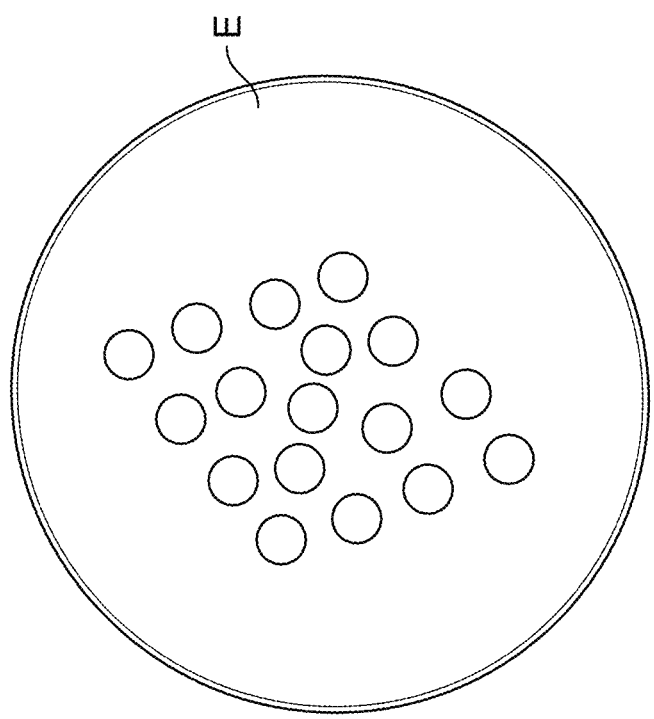
FIG. 12 illustrates an exemplary embodiment of an electrode suitable for use in the system of FIG. 1.

In embodiments, in order to ensure good contact with the user's skin, the receptacles 20a, 20b and 20c are mated with a "dry electrode" as noted above that include a surface with a plurality of raised bumps to contact the user's skin. FIG. 12 illustrates an example of such a dry electrode in which this surface is visible. In embodiments, the receptacles 20a, 20b and 20c, and thus the electrodes E mounted therein, are preferably positioned in alignment with the open portions of the adhesive element 60 such that they can contact the skin of the patient when the monitor 12 is adhered in place on the patient's body. In embodiments, where the monitor 12 is held in place using clothing, an opening may be provided in the clothing to allow the electrodes E in the receptacles 20a, 20b and 20c to contact the user's skin.

In an embodiment, the monitor 12 may include one or more LEDs 35 that are positioned to face the patient when the monitor is in contact with the patient. In a preferred embodiment, a red LED and an infrared LED are included as well as a light meter to detect reflected light from the LEDs. In embodiments, the LEDs 35 and light meter may be used to determine various parameters, including blood pressure, SPO2 and heart rate (pulse). In embodiments, blood pressure estimation may be determined based on pulse transit time (PTT), the interval between the peak of the R-wave in electrocardiogram (ECG) and the photoplethysmogram (PPG) measured elsewhere, which is related to arterial stiffness, and can be used to estimate the systolic blood pressure (SBP) and diastolic blood pressure (DBP). In embodiments, the pulse measurement may be obtained based on the use of reflected light from the LEDs. In embodiments, the pulse information in a conventional PTT calculation is gathered at the user's heart and second pulse information is gathered at a finger or other extremity. In the present application, the second pulse location may be in the proximity of the heart and chest as well since the monitor 12 must be positioned in that area to provide an accurate ECG. In embodiments, reflection of light from the LEDs 35a is used to determine pulse at the heart and spaced from the heart. In an embodiment, a modified PTT calculation is provided for estimating blood pressure in view of the close proximity of the two pulse points. In embodiments, this calculation may be performed by the monitor 12, the gateway 14 or elsewhere, such as the central processing location 16. Naturally, in embodiments, the LEDs 35a may be used to determine pulse of the patient as well. In addition, in embodiments, a thermistor 35b may be used to determine patient skin temperature.

In embodiments, the LEDs 35a are used to determine PPG of the patient. In this application, a modified algorithm is also used to allow for patients with darker skin color. PPG uses the amount of light reflected and those with darker skin colors may not reflect sufficient light such that the algorithm is modified to adjust for this.

In embodiments, the system 10 may also be used to determine the location or proximity of a patient. For example, as noted above, in embodiments, in an enterprise environment where multiple gateway devices 14 are positioned throughout a facility, patient proximity and location may be determined based on communication with a particular gateway device. In addition, in embodiments, nurses or other healthcare personnel may carry monitors 12, or variations thereof to track their interaction with particular patients based on their relative position. In embodiments, this may be used in order to ensure compliance with medication and therapy schedules.

In an embodiment, mobility information or proximity information may be used to determine the status of the patient, i.e. resting, walking, running etc. In embodiments, this information may be combined with information on the user's vitals to provide a more useful context for the patient information. For example, an elevated heart rate or blood pressure may not be a cause for alarm if the patient has just walked up a flight of stairs whereas it may be a danger sign if the patient is and has been laying still for some time. Thus, in embodiments, the state of the user is recorded along with the vitals. In embodiments, all of this information is preferably provided to the central monitoring station 16 and preferably to the clinical monitoring station 19. The clinical monitoring station 19 is typically a computing device provided in a hospital or other healthcare facility that analyzes information regarding the patient as would be the case if the patient were in the hospital. In embodiments, where the patient information indicates that the patient may be under duress, an alert may be generated and sent to healthcare providers, family members or emergency contacts. In embodiments, the clinical monitoring station 19 may make decisions based on current information and/or historical information and may also contact the emergency call center 18 to send an alert signal which is acted on as described above. In embodiments, the decisions discussed above may be made by the central station 16 or clinical monitoring station 19.

Figure 6:
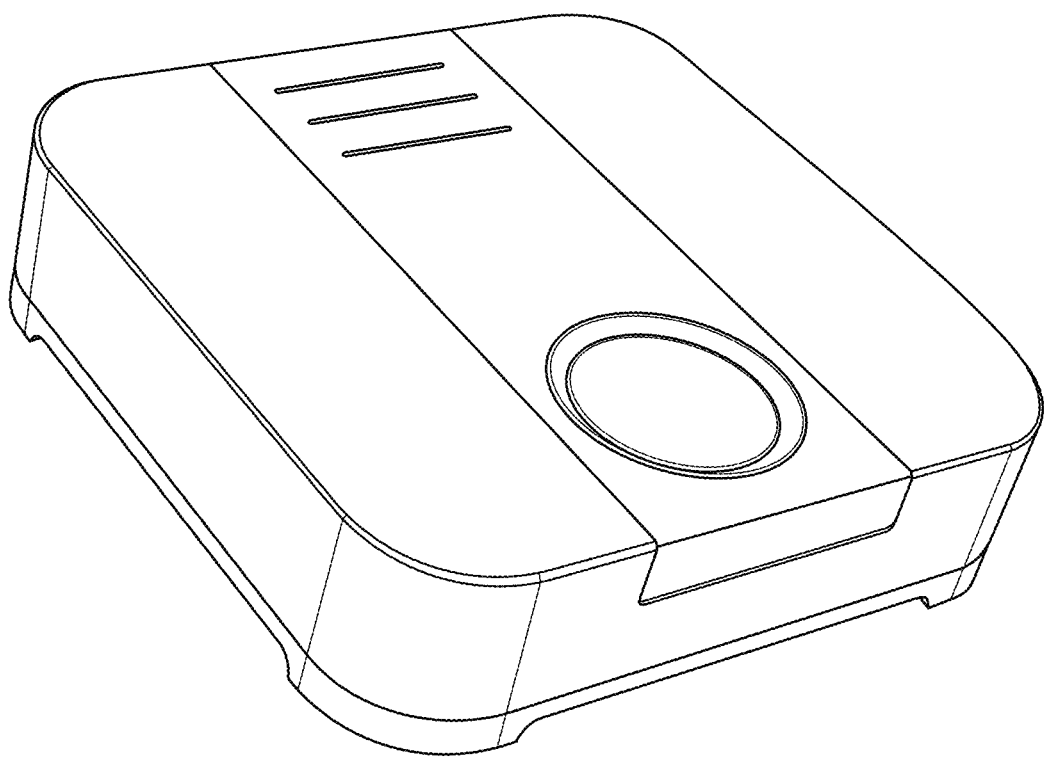
FIG. 6 is an exemplary embodiment of a gateway device used in the system of FIG. 1 in accordance with an embodiment of the present application.

In embodiments, the gateway 14 and monitoring device 12 communicate with each other via bidirectional radio communication such that the device sends data to the gateway and the gateway can send data or instructions to the device 12. In embodiments, the wireless communication between the gateway 14 and monitoring device 12 may be via light or sound, for example, using ultrasonic communication. In an embodiment, the gateway 14 may be programmable with a predetermined test such that a series of measurements may be initiated by pressing a single button or receiving a single command. In embodiment, the single command may be provided by the central station 16, for example. Similarly, in embodiments, the monitor 12 may be preprogrammed in such a manner. In embodiments, the monitor 12 may be programmed to perform desired measurements based on a command received from the central station 16, via the gateway 14. In embodiments, the gateway device 14 also communicates via radio frequency, other wireless communication system or a wired connection with the emergency call center 18, the central monitoring station 16 and clinical monitoring station 19 and allows two way communication such that the gateway can transmit information and can receive information and instructions. The gateway 14 may receive commands regarding taking certain measurement from the central station 16, for example. These commands may be executed by the gateway 14 or passed on to the monitor 12, as appropriate. In embodiments, the bidirectional communication between the gateway and the central station and/or between the gateway and the monitor 12 may be used to update firmware operating in the monitor or the gateway 14. In embodiments, as illustrated, in a preferred embodiment, data may be saved in a cloud setting, however, the data may be saved in any suitable storage element. In embodiments, the gateway 14 may include a display (see FIG. 6A, for example) that illustrates information regarding the user's vital signs or other bodily functions. In embodiments, data that is gathered by the monitor 12 may be checked or verified for errors or corruption before it is transmitted to the gateway 14 and/or the central station 16. If the data is flawed, in embodiments, it will not be transmitted. Similarly, in embodiments, data at the gateway 14 may be checked for errors or corruption before it is transmitted to either the monitor 12 or the central station 16 (or emergency call center 18 or clinical monitoring station 19). In embodiments, flawed data is not transmitted to avoid wasting resources on flawed data.

Figure 8:
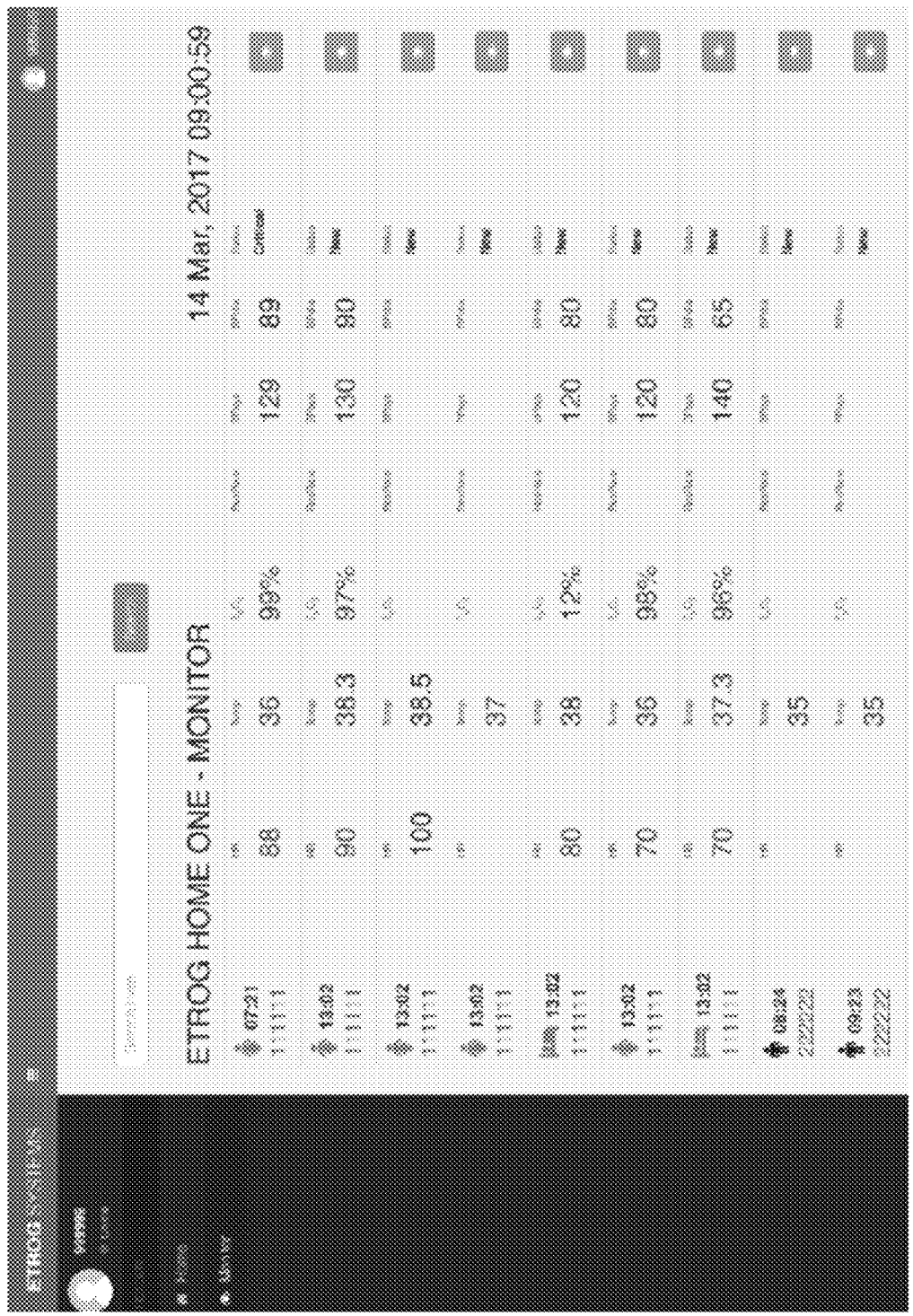
FIG. 8 is an exemplary screen shot illustrating an exemplary graphical user interface for displaying patient information provided by the system of FIG. 1.
Figure 9:
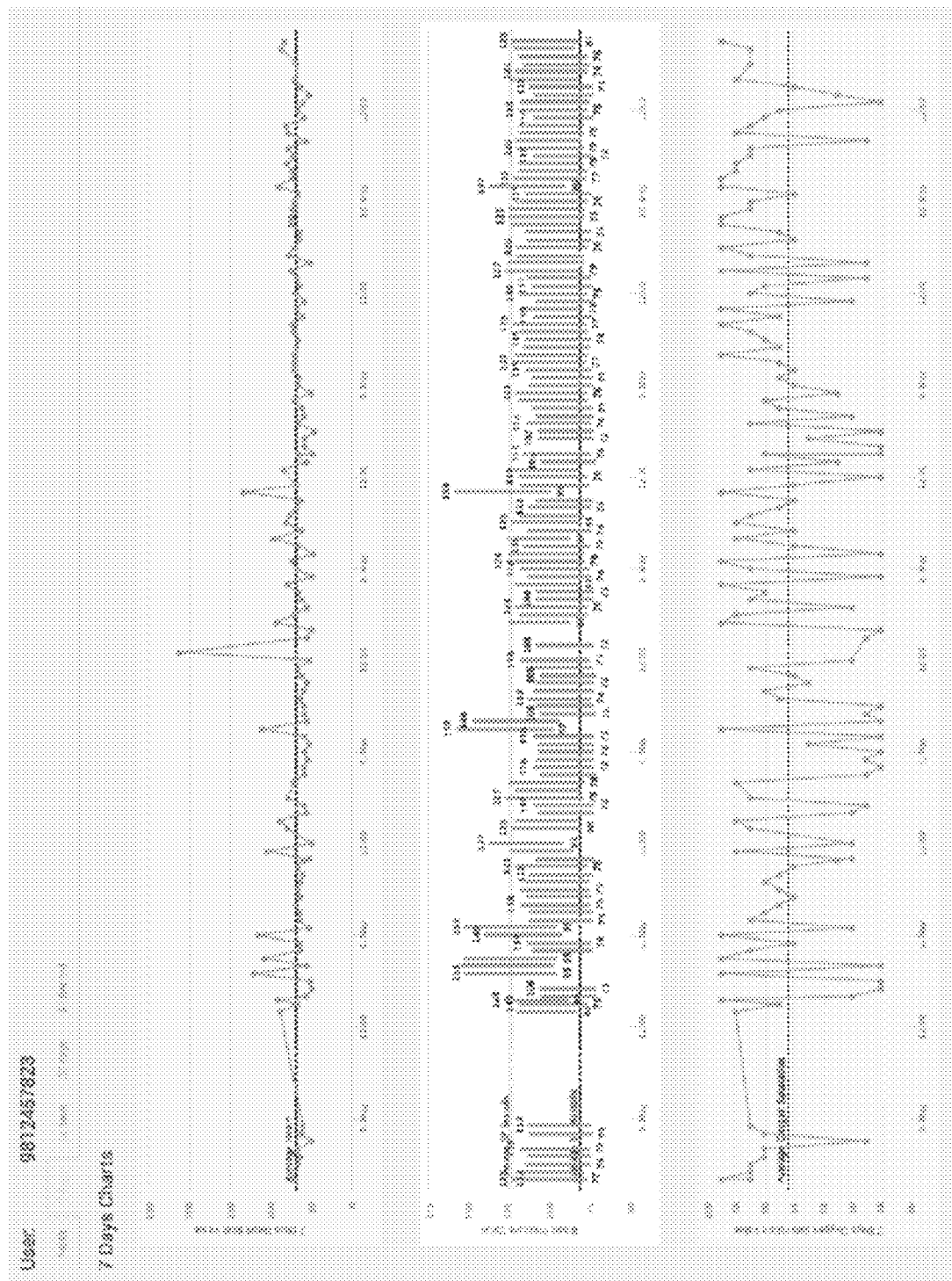
FIG. 9 is an exemplary screen shot illustrating an exemplary graphical user interface for displaying a historical record of certain patient information that was provided by the system of FIG. 1.

In embodiments, the central station 16 may include at least one computing device operably connected to at least one memory element and may store and archive data. In addition, the computing device of the central station 16 includes one or more processors that provide analysis of data including but not limited to the generation of predictive models based on past information for a patient. In embodiments, the data may be viewed by users at the central station 16, at the call center 18 or at the clinical monitoring center 19. In embodiments, the call center 18 and the clinical monitoring center 19 may include one or more computing devices operably connected to one or more memory devices. The computing devices also include one or more processors that may be used to process information received and to allow access thereto. In a preferred embodiment, specific users may select the information that they wish to view. In embodiments, information may be viewed in real time, or presented as part of a historical record or both. FIG. 8 illustrates an exemplary screen shot of a graphical user interface usable by a user to view certain patient information. FIG. 9 similarly illustrates an exemplary screen shot of a graphical user interface displaying historical data regarding a patient.

In an embodiment, the information provided by the monitoring device 12 and transmitted by the gateway device 14 is stored and analyzed to provide a vitality score. In embodiments, this may be done at the monitoring device 12, the gateway device 14, the central station 16, the call center 18 and/or the clinical monitoring center 19. In embodiments, the vitality score may generated based on the information regarding vital functions of the patient monitored by the monitoring device 12 with a higher vitality score assigned to patients with desirable results. In embodiments, patient's whose vital functions are observed to be in desirable ranges will be assigned higher vitality scores. In addition, certain functions may be weighted, if desired, to have more or less influence over the vitality score. In embodiments, this calculation is preferably done in the central station 16, but may be done elsewhere in the system 10.

Figure 11:
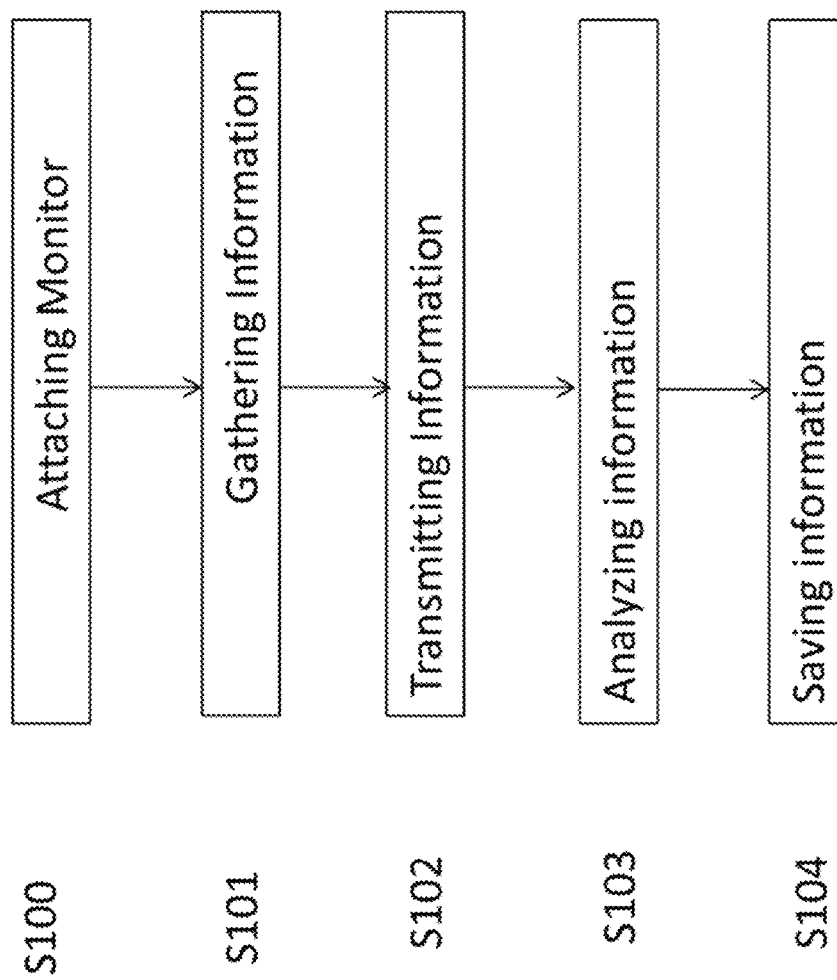
FIG. 11 is a is an exemplary flow chart illustrating a method for monitoring a user in accordance with an embodiment of the present disclosure.

FIG. 11 illustrates an exemplary flow chart for a method of monitoring a patient. In embodiments, in step S100, a monitoring element is attached to the patient's skin. In embodiments, in step S101, the monitoring element may provide information indicating various vital functions and other health related information of the patient. In embodiments, in step S102, the information indicating various vital functions of the patient is transmitted to an external monitoring element. In embodiments, in step S103, the external monitoring element may assess or otherwise analyze the information indicating various vital functions of the patient to determine whether the patient is in distress. In embodiments, this analysis may also take place locally at the monitor 12, gateway 14, central station 16, call center 18 and/or clinical monitoring center 19. In embodiments, if distress is determined, an alert signal may be generated and intervention may be requested. In embodiments, in step S104, the information indicating various vital functions of the patient may saved in a storage element or any suitable memory element. In embodiments, all of the information may be time stamped such that information regarding different patient functions may be matched to other information from the same time to provide an accurate snapshot of the patient's health at that time.

In embodiments, a calibration step may be provided after step S100 in which the monitoring element 12 and system 10 are calibrated. In embodiments, calibration may be accomplished by comparing measured or calculated values of the system 10 to values that are obtained using so called gold standard devices. In embodiments, the term "gold standard device(s)" generally refers to traditional devices used to measure body function. For example, with respect to blood pressure, a traditional blood pressure cuff is a gold standard device. In an embodiment, the cuff may be automated and provided with a transmission device such that the measured values thereof are transmitted to the monitor 12, gateway device 14, central monitoring center 16 or the clinical monitoring center 19 where they may be recorded and compared to measured or calculated values provided via the monitor 12 or other sensors in order to fine tune the system 10. Alternatively, in embodiments, blood pressure may be manually measured by a healthcare professional with the results may be either transmitted from a personal electronic device or otherwise input by the healthcare provider. In embodiments, another example of a "gold standard device" would be a thermometer for use in determining body temperature. In embodiments, this may be automated in a manner similar to that discussed above with respect to the blood pressure cuff or may be provided by intervention of a healthcare provider. In embodiments, the values measured by such gold standard devices are compared to the measured or calculated values determined by the system 10 to test the accuracy of the system. In embodiments, where there is a discrepancy, the system 10 may be modified to provide for better accuracy and/or the monitor 12 may be repositioned to provide better results. In embodiments, while a blood pressure cuff and thermometer are identified herein as "gold standard devices," it should be understood that there are many other devices that would be considered gold standard devices and this term is not limited to these two examples but includes any devices that are customarily and traditionally relied on by healthcare providers to gather information about patients and their body functions. In embodiments, these devices may be automated, as suggested above, or may be used manually by healthcare providers in order to properly calibrate the system 10. In embodiments, the calibration step discussed above may be repeated periodically, as desired, to maintain accuracy of the system 10. It is noted that the calibration step should always be executed when the monitor 12 is being used in conjunction with a new patient.

In an embodiment, the monitoring element in step S101 is the monitoring element 12 discussed above. In an embodiment, after step S101, the information indicating various vital functions of the patient may be transmitted from the monitoring element 12 to the gateway device 14 discussed above. In embodiments, the gateway device 14 may be used to complete step S102. In embodiments, the external monitoring element may be embodied by any of the central monitoring center 16, the emergency call center 18 or the clinical monitoring center 19 which may process the information indicating various vital functions of the patient as described above. In embodiments, the monitoring element of step S101 may include the in-bed monitoring element 90.

In embodiments, as noted above, one or more LEDs 35*a* on the element may be used to determine PPG, pulse, and blood pressure as part of step S101, if desired. Other patient information may be provided via other sensors, such as the thermistor 35*b* and others discussed above.

In embodiments, if desired, as noted above, a step of establishing a unique signature of the user may be provided after step S101 or step S102 or as part of the calibration step discussed above. Further, following the storage step of S104, in embodiments, the stored information may be accessed for further processing. In an embodiment, the stored information may be used to make predictive calculations regarding user vitals. For example, past data regarding vital signs may be useful in predicting and diagnosing diseases or disorders.

Figure 14:
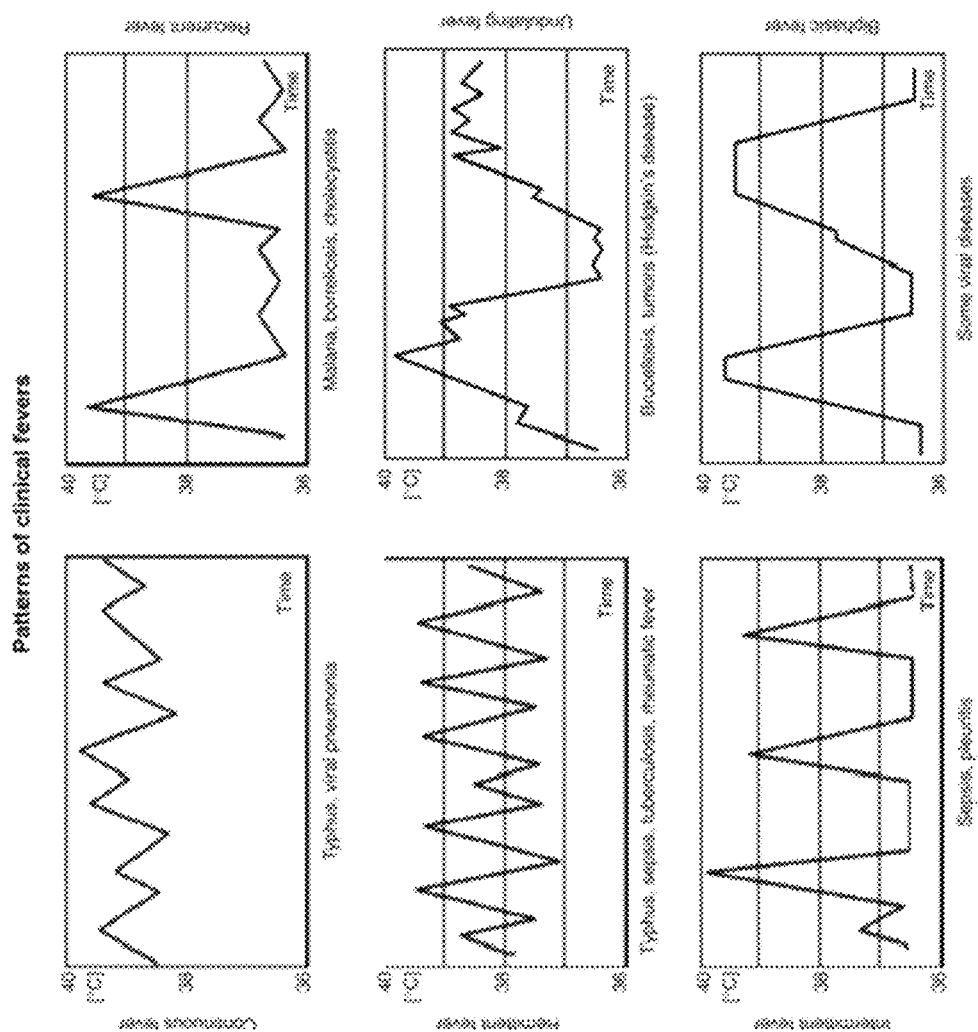
FIG. 14 illustrates a chart illustrating various fever patterns and certain diseases associated with those patterns.

FIG. 14 illustrates various fever patterns and indicates diseases that tend to result in such patterns. FIG. 15 illustrates a table describing some of these patterns and identifying diseases consistent with them. Accordingly, the stored information regarding user vital signs such as body temperature, for example, may be analyzed over a period of time to predict or help diagnose a particular disease of the user. While body temperature is discussed above, patterns may be identified with respect to other patient attributes which may also allow for prediction or diagnosing of disease. In embodiments, the stored information may be used for predicting and diagnosing disease by the central monitor 16, emergency call center 18 or the clinical monitoring center 19.

In addition, the stored information may be used to provide a vitality score, as mentioned above. In embodiments, the vitality score may be used to indicate a general trend in patient health, i.e. improving, degrading or neutral based on the information provided by the system.

The transmitted information may also be analyzed to determine whether intervention is required to aid the user. For example, in the event that the transmitted information includes a duress signal, as discussed above, an additional step of summoning intervention may be added. Alternatively, or in addition, a step of communicating with the user by voice may be added to check on the user's status before summoning intervention. In another embodiment, in the event that the transmitted information indicates that the user is in distress, i.e. dangerously low or high heart rate, blood pressure, pulse, body temperature, lack of mobility for an extended period of time etc., a decision may be made to summon intervention. In embodiments, these decisions may be made at the emergency call center 18, either automatically or based on human intervention, the clinical monitoring center 19 or the central monitoring center 16.

Although the present invention has been described in relation to particular embodiments thereof, many other variations and modifications and other uses will become apparent to those skilled in the art. Steps and units described in relation to one aspect of the method or system may be added, or substituted, for steps or units described with respect to another aspect of the system. Combinations and permutations of steps different from those outlined are also contemplated. Steps outlined in sequence need not necessarily be performed in sequence, not all steps need necessarily be executed, and other intervening steps may be inserted. It is preferred, therefore, that the present invention be limited not by the specific disclosure herein.

What is claimed is:

1. A system to monitor a user's health comprising:
   a monitor element securable to and in contact with the user's body at any desired position, the monitor element including at least one sensor providing information associated with health of the user, the sensor providing information associated with one or more of:
   user heart rate;
   user respiration rate;
   user blood pressure;
   user oxygen level;
   the sensor including:
   at least one light emitting diode;
   at least one light sensor facing the user, wherein the at least one light sensor provides light sensing information based on light reflected from the at least one light emitting diode off the user's skin; and
   a bed sensor configured to provide position information associated with a position of the user in a bed;

a central station in communication with the monitor element, wherein the information associated with health of the user and position information are received by the central station via radio frequency communication, wherein the central station analyzes the information associated with health of the user and position information and determines whether intervention is appropriate, based at least one of:
at least one heartrate threshold;
at least one respiration rate threshold;
at least one blood pressure threshold based on at least the light sensing information; and
at least one oxygen level threshold.

2. The system of claim 1, wherein the information associated with the health of the user is stored in a memory associated with the central station.

3. The system of claim 1, wherein the information associated with the health of the user further comprises information associated with:
user weight;
user activity; and
user sleep quality.

4. The system of claim 1, wherein the monitor element comprises an adhesive element positioned on an inner surface thereof for contact with the user's skin to position the monitor element on the user's body.

5. The system of claim 4, wherein the adhesive element includes an alignment element positioned to aid in positioning of the monitor element on the user's body.

6. The system of claim 1, wherein the monitor element comprises a plurality of electrodes.

7. The system of claim 6, wherein a pair of electrodes are provided on a first end of the monitor element and a third electrode is provided on a second end of the monitor element, opposite the first end.

8. The system of claim 7, wherein the pair of electrodes are provided side by side.

9. The system of claim 8, wherein the third electrode is spaced a predetermined distance from the pair of electrodes.

10. The system of claim 9, wherein the pair of electrodes and third electrode are positioned to provide ECG information.

11. The system of claim 7, wherein the first end of the monitor element is connected to the second end of the monitor element via a flexible bridge element such that the first end of the monitor element and second end of the monitor element are movable with the user's skin relative to each other.

12. The system of claim 1, wherein the position information indicates a presence of the user in the bed.

13. The system of claim 1, wherein the light sensing information and ECG information are used by the monitor to determine the user blood pressure.

14. The system of claim 1, wherein the light sensing information and ECG information are transmitted from the monitor element to the central station and the user blood pressure is determined at the central station.

15. The system of claim 1, further comprising an alert device in wireless communication with the central station.

16. The system of claim 15, wherein the alert device comprises an alert button, wherein the alert device transmits an alert signal to the central station when the alert button is actuated.

17. The system of claim 16, wherein the central station transmits the alert signal to emergency personnel.

18. The system of claim 16, wherein the alert device provides two way communication with the central station.

19. The system of claim 1, wherein the position information is used by the central station to provide mobility information associated with the user.

20. The system of claim 1, wherein the position information is used by the central station to provide sleep activity information associated with the user.

21. The system of claim 1, wherein the monitor element checks the information associated with health of the user for errors prior to sending the information associated with health of the user to central station and does not send the information associated with health of the user to the central station when errors are detected.

22. The system of claim 1, wherein the monitoring device is in two way communication with the central station.

\* \* \* \* \*